(12) United States Patent
Hansen (10) Patent No.: US 10,426,876 B2
(45) Date of Patent: Oct. 1, 2019

(54) BREST PUMP DEVICE

(71) Applicant: Vesucta ApS, Aarhus N. (DK)

(72) Inventor: Jan Erik Vest Hansen, Aarhus C (DK)

(73) Assignee: Vesucta ApS, Aarhus N (DK)

( * ) Notice: Subject to any disclaimer, the term of this patent is extended or adjusted under 35 U.S.C. 154(b) by 590 days.

(21) Appl. No.: 15/029,109

(22) PCT Filed: Oct. 9, 2014

(86) PCT No.: PCT/EP2014/071660
§ 371 (c)(1),
(2) Date: Apr. 13, 2016

(87) PCT Pub. No.: WO2015/055503
PCT Pub. Date: Apr. 23, 2015

(65) Prior Publication Data
US 2016/0256617 A1    Sep. 8, 2016

(30) Foreign Application Priority Data

Oct. 14, 2013 (EP) ..................................... 13188421

(51) Int. Cl.
*A61M 1/06* (2006.01)
*A61M 1/00* (2006.01)
*A61J 9/00* (2006.01)

(52) U.S. Cl.
CPC ................ *A61M 1/066* (2014.02); *A61J 9/00* (2013.01); *A61M 1/0066* (2013.01); *A61M 1/06* (2013.01);
(Continued)

(58) Field of Classification Search
CPC ....... A61M 1/062; A61M 1/06; A61M 1/0066
See application file for complete search history.

(56) References Cited

U.S. PATENT DOCUMENTS

| 4,643,719 A | 2/1987 | Garth |
| 4,795,428 A | 1/1989 | Hwang |

(Continued)

FOREIGN PATENT DOCUMENTS

| AU | 2011 301 698 A1 | 3/2013 |
| CN | 201996891 | 10/2011 |

(Continued)

OTHER PUBLICATIONS

European Patent Office, Written Opinion of the International Preliminary Examining Authority issued in International Application No. PCT/EP2014/071660 dated Sep. 18, 2015.

(Continued)

*Primary Examiner* — Imani N Hayman
*Assistant Examiner* — Tiffany Legette
(74) *Attorney, Agent, or Firm* — Wood Herron & Evans LLP (57) ABSTRACT

The invention relates to a breast pump kit comprising a breast pump collection system which is to be replaceable and detachable connected to an electrical driving unit during use. The breast pump collection system comprises a breast shield for placing on a breast of a user, a pump unit, and tubing connecting the breast shield to the pump unit. The pump unit comprises a compartment of a variable volume in fluid connection to the exterior only via the tubing. The pump unit is configured to be detachable combined to the driving unit such that a driving motion of the driving unit acts to alternatingly expand and contract the compartment of the pump unit. In this way the pump unit creates alternating suction and pressure in the breast shield and at the breast of the user when in use. The invention further relates to a breast pump collection system for use in such breast pump kit.

13 Claims, 6 Drawing Sheets

(52) U.S. Cl.
CPC ....... *A61M 1/062* (2014.02); *A61M 2205/071* (2013.01); *A61M 2207/00* (2013.01)

(56) References Cited

U.S. PATENT DOCUMENTS

| | | | |
|---|---|---|---|
| 5,007,899 A | 4/1991 | Larsson | |
| 5,165,866 A | 11/1992 | Kato | |
| 5,304,129 A | 4/1994 | Forgach | |
| 8,992,467 B2 | 3/2015 | Kobayashi | |
| 2001/0038799 A1 | 11/2001 | Silver et al. | |
| 2003/0073951 A1* | 4/2003 | Morton | A61B 5/6834 604/73 |
| 2004/0158199 A1* | 8/2004 | McKendry | A61M 1/0066 604/74 |
| 2005/0085768 A1* | 4/2005 | Greter | A61M 1/06 604/74 |
| 2007/0060873 A1 | 3/2007 | Hiraoka et al. | |
| 2008/0275386 A1* | 11/2008 | Myers | A61M 1/06 604/74 |
| 2009/0087860 A1* | 4/2009 | Todd | C07K 16/3069 435/7.1 |
| 2010/0003016 A1 | 2/2010 | Tout et al. | |
| 2010/0030166 A1 | 2/2010 | Tout et al. | |
| 2010/0130921 A1* | 5/2010 | Kobayashi | A61M 1/06 604/74 |
| 2010/0292636 A1 | 11/2010 | Renz et al. | |
| 2012/0265169 A1* | 10/2012 | Sherman | A61M 1/06 604/514 |
| 2013/0197475 A1* | 8/2013 | Dunn | A61M 5/2033 604/506 |

FOREIGN PATENT DOCUMENTS

| | | |
|---|---|---|
| CN | 102470203 | 5/2012 |
| CN | 202740492 | 2/2013 |
| WO | 2012/034238 A1 | 3/2012 |

OTHER PUBLICATIONS

European Patent Office, International Search Report and Written Opinion issued in International Application No. PCT/EP2014/071660 dated Jan. 8, 2015.
European Patent Office, European Search Report issued in Application No. EP 13 18 8421 dated Feb. 27, 2014.
European Patent Office, International Preliminary Report on Patentability issued in International Application No. PCT/EP2014/071660 dated Jan. 21, 2016.

* cited by examiner

BREST PUMP DEVICE

FIELD OF THE INVENTION

The present invention relates to a breast pump collection system. The invention also relates to a breast pump kit of a breast pump collection system and a separate driving unit.

BACKGROUND

Different types of breast pumps exist to aid in extracting milk from the breasts of lactating women. Breast pumps may be manual devices powered by hand or foot movements, or powered electrical devices where a breast shield via tubing is coupled to a pump motor powered by mains electricity or batteries.

Most breast pumps allow direct collection of pumped breast milk into a container that can be used for storage and feeding. The plastic tubing and breast shield of a breast pump is commonly referred to as the collection system.

Different types of pump motors are used in breast pumps to create the suction such as piston pumps or rotary vane pumps. In order to avoid a free passage of air as well as to prevent any contamination or overflow into pump motor, a bacteria filter, a diaphragm or some kind of barrier must be inserted in the tubing between the breast shield and the connection to the pump motor. In this design, the suction of the pump motor lifts the diaphragm to create a vacuum within the collection system to extract milk. However the diaphragm or filter causes a considerable reduction in the suction obtainable at the breast compared to the suction at the exit of the pump motor. Also, the diaphragm or filter tends to deform differently from suction cycle to suction cycle which then lead to changes in the obtained suction and difficulties in controlling the suction level.

Another drawback of the known apparatus is the level of noise emitted by the pump motor which decreases the user comfort.

DESCRIPTION OF THE INVENTION

It is therefore an object of embodiments of the present invention to overcome or at least reduce some or all of the above described disadvantages of the known breast pumps by providing a breast pump collection system which may be operated at a very low noise yet with efficient pumping effect.

It is a further object of embodiments of the invention to provide a breast pump which may be simple yet effective to prepare for use, operate, and dismantle after use.

It is a yet further object of embodiments of the invention to provide an effective device of a minimal number of parts and which may be manufactured fastly by a minimum of operations and a low manufacturing cost.

A further object of embodiments of the invention is to provide a breast pump collection system which may be used as a single-use disposable product and may be manufactured at such low cost as to promote single-use.

Yet a further objective is to provide a breast pump with enhanced suction and enhanced control of the delivered suction.

In accordance with the invention this is obtained by a breast pump collection system to be detachable combined to an electrical driving unit when in use thereby forming a breast pump kit. The breast pump collection system comprises a breast shield for placing on a breast of a user, a pump unit, and a tubing connecting the breast shield to the pump unit. The pump unit comprises a compartment of a variable volume in fluid connection to the exterior only via the tubing and the pump unit is configured to be detachable combined to the driving unit such that a driving motion of the driving unit acts to alternatingly expand and contract the compartment of the pump unit, the pump unit thereby creating alternating suction and pressure in the breast shield and at the breast of the user when in use.

Hereby is obtained a breast pump with reduced and very minimal noise emission as the breast pump collection system unlike traditional models is not to be connected to a vacuum pump for creation of the suction. Rather the expansion of the compartment in the pump unit creates the suction when driven by or activated by a driving unit. Hereby the number of movable parts is considerably reduced and as the need for a gear, transmission belt, and other transmission parts is avoided. This both reduces the noise emission considerably and reduced any energy loss by the system. The low noise of the breast pump when in use acts to increase the user comfort.

Preferably, the breast pump collection system and the driving unit are completely separate parts only to be combined by the user when to be used.

As the compartment of a variable volume is in fluid connection to the exterior only via the tubing, the pump unit does not comprise any other openings, vents, valves or the like to the exterior. Hereby the pump unit forms a closed system only connected to the exterior via the tubing, which means that no air or fluid can be exchanged with any machine parts of the driving unit or with the ambient during use of the breast pump. Hereby the risk of infections is greatly reduced and at the same time the risk of getting milk in the mechanics of the driving mechanism is removed. As the compartment is closed, this further makes it possible to rinse, wash, or sterilize the breast pump collection system if desired without any risk of the water or detergent getting into the driving system. In this way the breast pump collection system can even be rinsed or sterilized with very hot water while combined to and driven by the driving unit. Alternatively, the breast pump collection system can be rinsed or sterilized while separated from the driving unit. In this way the breast pump collection system can advantageously be effectively cleaned and the risk of infections minimized even if the collection system is used multiple times.

Preferably, however, the pump unit is a single-use and disposable component which is advantageous in ensuring high hygiene and minimising the risk for infections. In some hospitals single-use products are even a requirement to ensure the necessary high hygienic standards necessary when caring for babies and especially newly born and preterm babies with reduced immune systems. Such single-use components or products are made possible and economically feasible due to the very few parts of the breast collection system and the very few parts to be assembled reducing the manufacturing costs considerably. Further, this make the system more robust and simple yet effective to prepare for use, operate, and dismantle after use. This further makes the breast collection system suitable as an integrated single-use and disposable product which may be sold and delivered as a complete assembled ready-to-use system. These features are also very advantageous in reducing the time and thereby the costs to nursing staff and caring assistance. All in all is obtained a product with an increased hygiene and considerably lower risk for infections and contaminations which is extremely important especially for use in hospitals or in relation to milk extraction for preterm or newly born babies with reduced immune systems.

This system of the compartment being in fluid connection to the exterior only via the tubing is further advantageous in that hereby the breast pump does not need and has no membrane or diaphragm separating the breast side and the pump unit side. In other prior art breast pumps such diaphragm is paramount to ensure the hygienic and to prevent outside air from contaminating the expressed in order to preserves the milk's purity. As the breast collection system according to the invention does not need and has no such diaphragm or barrier is obtained firstly a very simple system with fewer parts and fewer parts to be assembled. Secondly is obtained a system with increased suction capability and where the same suction can be established repeatedly in each suction cycle, which is otherwise a problem in conventional system as the diaphragms both reduce the obtained suction and are prone to deform differently once in a while during a pumping sequence thereby causing the suction level during the pumping sequence. By the closed system according to the invention, the suction obtained by the expansion of the compartment is approximately the same as the suction in the breast shield without any significant loss. This further enables a reliable and precise control of the obtained suction or pressure at the breast of the user not only at the beginning but at each step all the way through a pumping sequence. Further, due to the increased efficiency of the system with no or only minimal suction loss from the pump unit to the breast of the user, a reduced force is needed to drive the pump unit which further reduce the noise emission of the breast pump.

Furthermore, the breast pump kit is advantageous in providing a driving unit for multiple uses and a breast collection system which can be preferably a single-use disposable system or optionally exchanged as often as desired. The breast collection system is advantageously completely separate to the driving unit thereby ensuring that no fluid from within the breast pump collection system can enter the driving unit or vice versa. Further, the breast pump kit is advantageous in that the suction is created by a driving unit in contrast to the known conventional systems where the tubing is coupled to a permanent pump which comprises more movable parts, is heavier, has a higher power consumption, and a higher noise level. In an embodiment of the breast pump collection system the pump unit comprises a bellows. Hereby is obtained a pump unit with a flexible volume by simple yet effective means and which can be manufactured for example by blow moulding in one or very few parts. Further, a bellows is advantageous in providing near complete compression and emptying during the contraction of the compartment with low force requirements. As approximately all air can be pressed out of the compartment a maximal suction can be created by the subsequent extraction. A bellows is furthermore advantageous as it folds in and out in a well-defined given way during each cycle of extraction and contraction. Further, by the use of a bellows, a direct and accurate control of the obtained suction and/or pressure and of the pumping sequence can be obtained simply by controlling or adjusting the stroke length and the frequency of the driving motion and without any need for measurements or pressure sensors. The obtainable suction is given directly by the dimensions of the bellows.

A further advantage of the pump unit comprising a bellows is that the bellows provide an automatic safety against too high suctions, as the dimensions of the bellows can be chosen such that the bellows will collapse and unfold if a certain pre-set suction is exceeded. In this way the suction will not be increased further even if the bellows is extended further.

The bellows is further advantageous in also enabling the pump unit to be operated manually for a shorter period of time, optionally by means of scissor-like structure or foot pedal, for example in case of power shortage of failure of the driving unit. Hereby is obtained an increased security and safety for the user.

The bellows is further relatively easy to rinse by being squeezed together a couple of times. This may advantageously be done with the tubing attached to the pump unit, thereby rinsing the tubing in the same operation. The rinsing may be performed with the pump unit combined to and driven by the driving unit or by manual squeezing of the bellows.

In an embodiment, the pump unit comprises a bellows of a number of folds in the interval of 1-30 folds such as 5-20 folds. Hereby may be chosen a bellows yielding appropriate stiffness or resistance and volume for the stroke length chosen or given by the driving unit and depending on the material of the bellows.

The bellows may preferably be of a volume in the range of 30-60 ml realized by a bellows of a diameter in the range of 30-40 mm and a length of 60-120 mm when extracted and of 20-50 mm when compressed. Hereby is obtained suction in the range of 0-330 mmHg. By choosing a bellows of the above mentioned dimensions and made of PE, which is a relatively soft material, is obtained that a suction of approximately 330 mmHg cannot be exceeded as the bellows then gets unstable and collapses if extended further. Hereby the user of the breast pump is secured against too high levels of suction, which can otherwise lead to tissue damage, discomfort, and pain.

The instability of the bellows in general occurs at given pressure/suction causing the folds to attain a reduced angle relative to the centre of the bellows. If the bellows then at this suction level is extracted further, the bellows collapses.

In an embodiment, the breast pump collection system comprises two breast shields connected to the same pump unit via tubing. Hereby is obtained that a user can milk from two breasts at the same time with the use of only one and the same driving unit as if only using one breast shield. To obtain an increased suction required to milk from two breasts at the same time, the stroke or driving length can be increased by the driving unit.

Alternatively, a driving unit can be configured to be detachable combined to two separate breast collection systems according to the invention. This is advantageous in allowing the user to apply different user settings to each of the breast collection systems.

According to an embodiment, the breast pump collection system further comprises a bottle fluidly connected to the breast shield. Hereby the milk can easily be collected in the bottle during milking. The system may further comprise a one-way valve such as for example a duckbill valve placed for the milk to pass into the bottle and a venting opening on the bottle side of the one-way valve. In this way the extraction of the compartment creates a suction in the breast shield at the breast of the user whereas a compression of the compartment presses the air through the one-way valve and out, and as such does not create any over-pressure at the breast.

In a further embodiment the pump unit is manufactured as a single-unit component. Hereby the collection system comprises only a minimal number of parts enabling the system to be manufactured fastly and by a minimum of operations thereby reducing the manufacturing cost. By manufacturing the pump unit as a single-unit component is further reduced or removed the risk of leaks to exterior so that the need for a membrane, filter or diaphragm separating the pump unit and breast shield side is removed.

In an embodiment of the invention, the pump unit is made of a thermoplastic material such as PE or TPE. The pump unit may be manufactured by blow moulding. Hereby the breast pump collection system can be manufactured at a low cost and the system can be made as a disposable unit used only one or alternatively very few times.

The pump unit, the tubing and the breast shield may in one embodiment be made of the same material, which makes the breast collection system more advantageous for recycling for example by granulation.

In an embodiment, the driving unit comprises at least two attachment means placed with a distance changing by the driving motion of the driving unit, and wherein the pump unit is configured to be combined to the driving unit by placing the pump unit in engagement with the attachment means. Hereby is obtained very simple means for the user to combine and afterwards detach the pump unit to the otherwise separate driving unit. The insertion and detachment of the pump unit can hereby be performed easily and fast by the fingers with no need for tools or strong hands. Further, the insertion and detaching is straightforward and intuitively simple with no need for instructions and minimal risk of doing it wrong. The attachment means may simply comprise an element with a cut-out or opening into which the pump unit can be inserted.

In an embodiment, the driving unit of the breast pump kit comprises a stepper motor. Hereby the number of transmission parts and movable parts in the breast pump kit is kept to a minimum and gears, transmission belts etc. are obviated. Hereby the energy loss is kept to a minimum and the noise emission of the driving unit and thereby of the breast pump is reduced considerably which increases the user comfort considerably.

A stepper motor is furthermore advantageous in providing a stroke length and velocity which may be easily set and controlled. These parameters of the stepper motor and of the driving unit may be pre-programmed or may be controllable by the user or adjusted before or during use of the breast pump.

In an embodiment the breast pump kit further comprises a control system for controlling the driving unit. The control system may be configured to control a stroke length and/or a frequency of the driving motion of the driving unit. In this way the suction level as well as the rhythm of the pumping sequence may be pre-set or adjusted during use by a user. Hereby the driving unit can be controlled to provide the optimal suction and the optimal suction rhythm for each individual user.

In an embodiment the driving unit further comprises a sensor for detecting the stroke length or the position of the driving unit and thereby of the extraction of compartment of the pump unit. Hereby the created suction can be precisely controlled by the motion of the driving unit.

In a further aspect, the invention relates to a breast pump collection system for use in a breast pump kit according to any of the above. The advantages hereof are as mentioned in relation to the breast collection system.

BRIEF DESCRIPTION OF THE DRAWINGS

In the following different embodiments of the invention will be described with reference to the drawings, wherein.

DETAILED DESCRIPTION OF THE DRAWINGS

Figure 1:
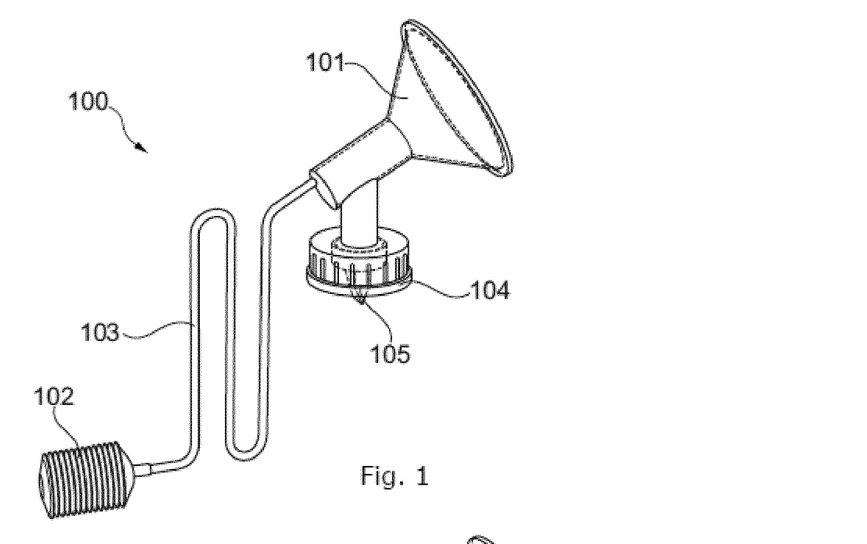
FIGS. 1 and 2 illustrate an embodiment of a breast pump according to the invention in two different stages of the pumping.
Figure 2:
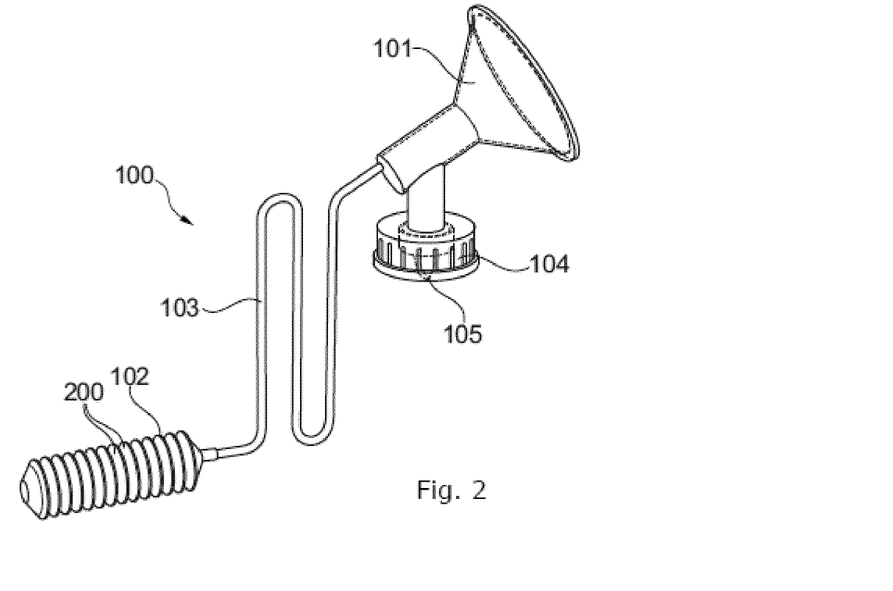

FIGS. 1 and 2 show an embodiment of a breast pump collection system 100 at two different stages of a pumping sequence. The breast pump collection system 100 comprises a breast shield 101 to be placed on the breast of the used and connected to a pump unit 102 via a tubing 103. The breast shield 101 is configured to be screwed 104 onto a collection bottle (not shown). At or on the opening into the bottle is placed a one-way valve 105 which here is a duckbill valve. The pump unit 102 in this embodiment is a bellows with a number of folds 200. In FIG. 1 the bellows is compressed. As the bellows is extracted as shown in FIG. 2 is created a suction to extract the milk from the breast.

Figure 3:
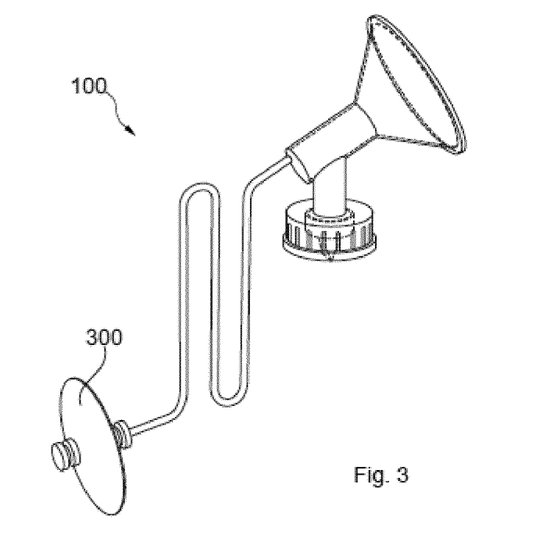
FIG. 3 illustrates a breast pump according to another embodiment of the invention.

In FIG. 3 is shown an embodiment of a breast collection system wherein the pump unit comprises a bellows 300 with a single fold.

Figure 4:
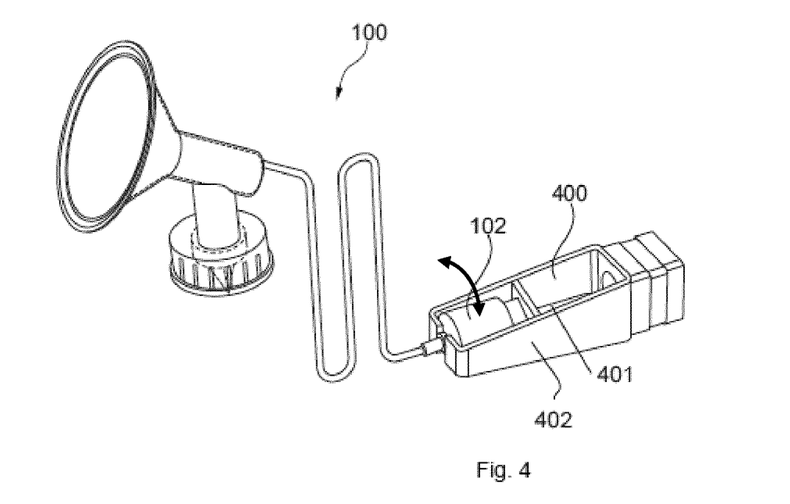
FIGS. 4 and 5 illustrate an embodiment of a breast pump as activated by a driving unit.
Figure 5:
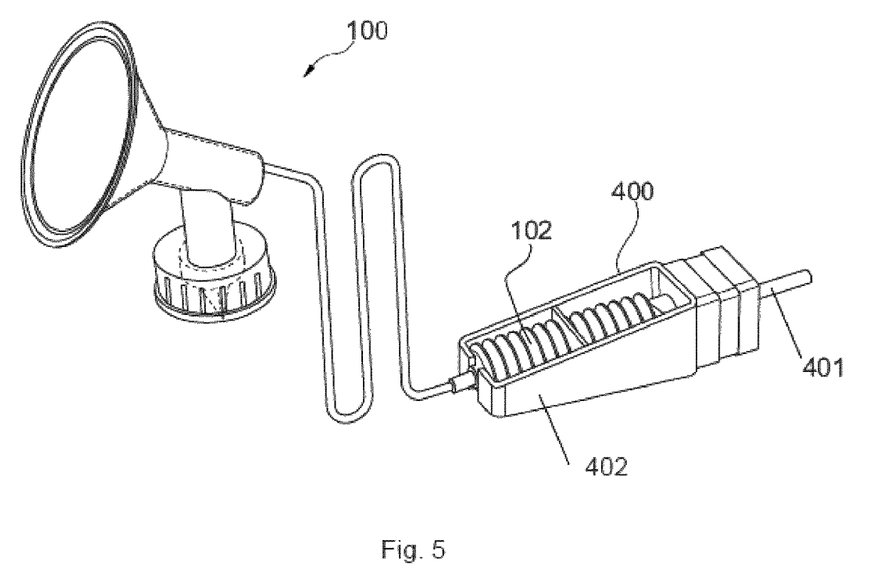
Figure 6A:
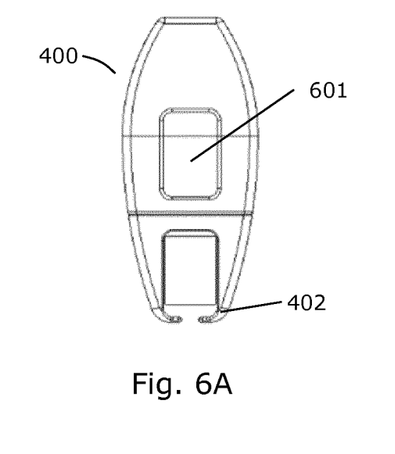
FIGS. 6A and 6B illustrate a driving unit for a breast pump kit according to an embodiment of the invention as seen from a side and in a perspective view, respectively.
Figure 6B:
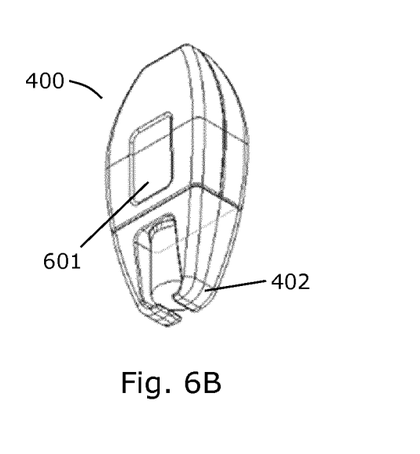
Figure 7A:
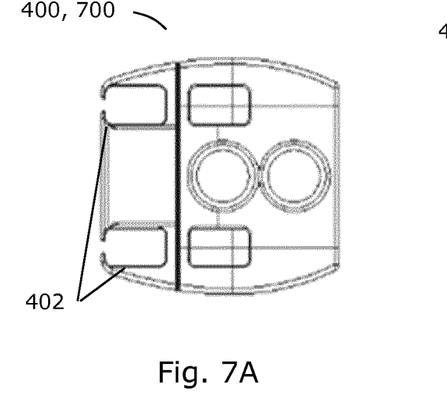
FIGS. 7A and 7B illustrate a driving unit of a breast pump kit for a double breast collection system according to an embodiment of the invention as seen from a side and in a perspective view, respectively.
Figure 7B:
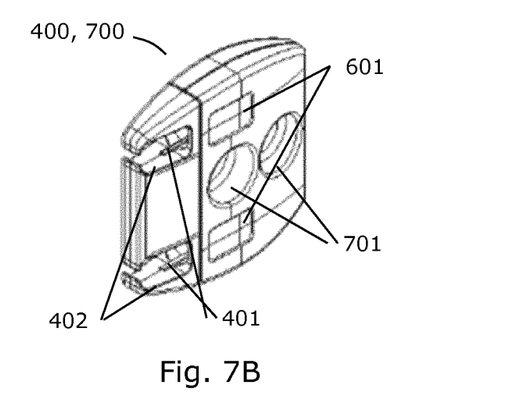

FIGS. 4 and 5 show the breast collection system 100 combined to a driving unit 400 which provides the driving motion for extracting (FIG. 5) and compressing (FIG. 4) the pump unit 102. The breast selection system and the driving unit together form a breast pump kit. In preparation to use the breast pump, the pump unit is simply inserted into a holder 402 wherein one end of the bellows is fixated and the other end is connected to a spindle 401 which is moved back and forth by the driving unit. The spindle is preferably driven by a stepping motor.

As can be seen in FIGS. 1-5 the pump unit forms a closed system and is only connected to the exterior via the tubing. Therefore the breast collection system does not need any filters, diaphragms or the like to ensure that the air or fluid within the system cannot leak out into the mechanical parts of the driving unit, as well as the air and fluid within the collection system cannot be contaminated during use.

Figure 8A:
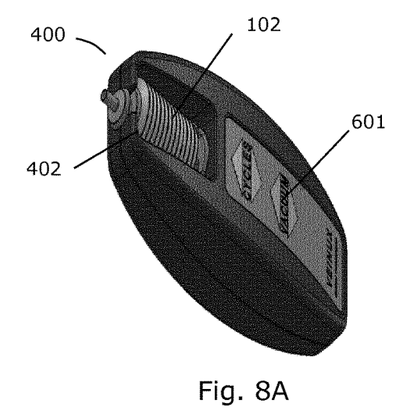
FIGS. 8A and 8B illustrate a driving unit for a breast pump kit according to an embodiment of the invention as seen from above and in a perspective view with the top casing of the drive unit removed, respectively.
Figure 8B:
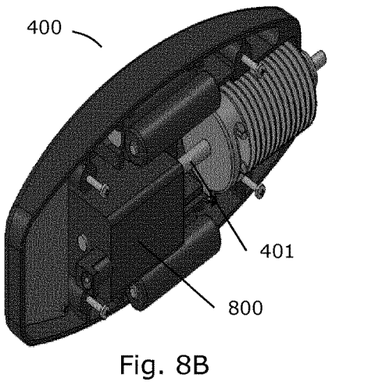

FIGS. 6A and 6B, and 8A and 8B illustrate embodiments of a driving unit 400 for a breast pump kit. The same driving unit is seen from one side in FIG. 6A and in a perspective view in FIG. 6B. In FIGS. 8A-B is seen a driving unit 400 with a pump unit 102 inserted and ready for use as seen from above and in a perspective view with the top casing of the drive unit 400 removed, respectively. The pump unit 102 of a breast collection system is inserted into the holder 402 and thereby temporarily attached to the driving means 401 of the driving unit. The user can adjust and control the suction level (via the stroke length) and the frequency (via the velocity of the driving unit) of the suction sequence via a control panel 601. The driving units of FIGS. 6 and 8 are configured to be used in combination with a single breast pump collection system as for example shown in FIGS. 1-4. In FIG. 8B can be seen the step motor 800 driving the spindle 401 such as to alternatingly compress and extend the bellows 102.

Figure 9A:
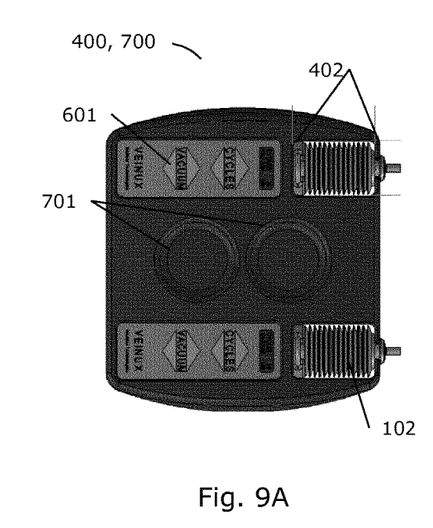
FIGS. 9A and 9B illustrate a driving unit of a breast pump kit for a double breast collection system with a pump unit inserted and according to an embodiment of the invention as seen from the top and in a perspective view with the top casing of the drive unit removed, respectively.
Figure 9B:
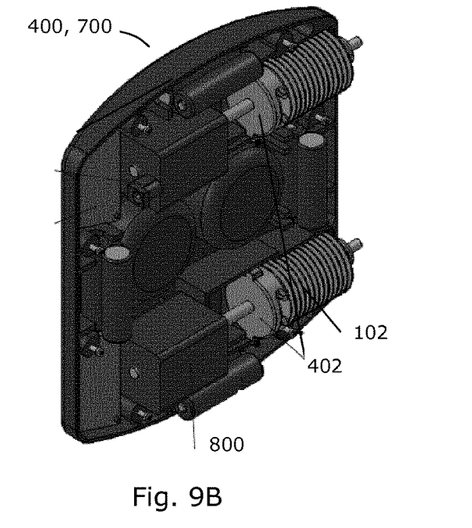
Figure 10:
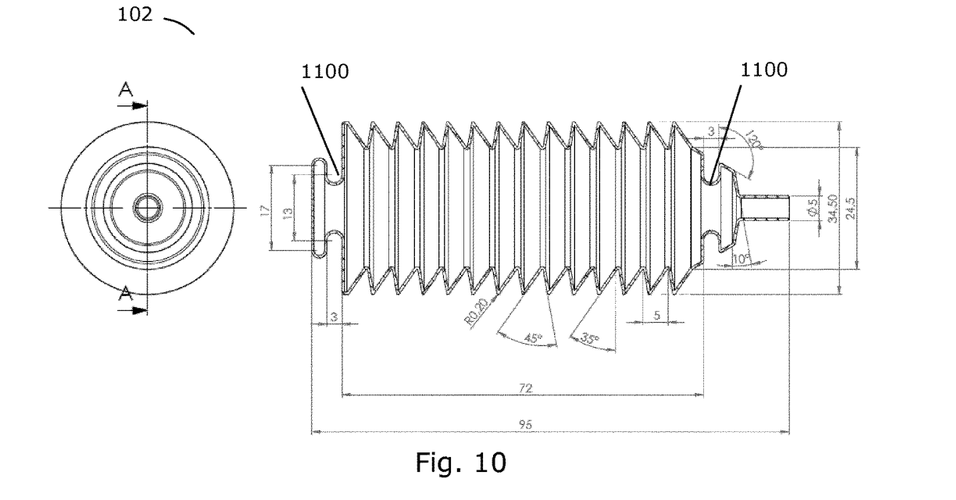
FIGS. 10 and 11 illustrate an embodiment of a pump unit with a bellows as seen in a cross-sectional view, from a side, and in a perspective view, respectively.
Figure 11:
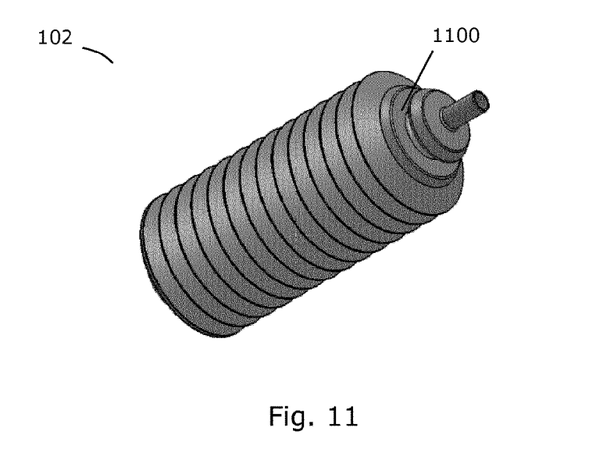

In FIGS. 7A-B and 9A-B are shown a driving unit 700 for driving two separate breast pump collection systems at the same time or separately. The same driving unit is seen from one side in FIG. 7A and in a perspective view in FIG. 7B. In FIG. 9A-B is seen a driving unit 400 with a pump unit 102 inserted and ready for use as seen from above and in a perspective view with the top casing of the drive unit 400 removed, respectively. The driving unit here comprises two holders 402 for detachably receiving the pump units of two collection systems. The driving unit may equally well be used to operate only one collection system if desired. The two collection systems may be operated and controlled separately and receive different control parameters by the user via the control panels 601. The driving unit may advantageously comprise one or two indentations or holes 701 wherein the collection bottles may be placed when not in use. In FIG. 9B can be seen the two step motors 800 driving the spindles 401 such as to alternatingly compress and extend the bellows 102. FIGS. 10 and 11 illustrate an embodiment of a pump unit 102 with a bellows as seen in a cross-sectional views, and in a perspective view, respectively. The bellows forms the compartment of variable volume. At opposite end portions of the bellows are formed bottleneck or narrowing portions 1100 which are placed in corresponding holders 402 in the drive unit. As one or both holders in the drive unit are moved back and forth, the bellows is compressed and extended correspondingly.

The shown bellows can provide near complete compression and emptying during the contraction of the compartment and approximately all air can be pressed out of the compartment. Thereby a maximal suction can be created by the subsequent extraction. The bellows is advantageous as it folds in and out in a well-defined given way during each cycle of extraction and contraction. In this way, the amount of suction and/or pressure can be controlled accurately by controlling or adjusting the stroke length and the frequency of the driving motion and without any need for measurements or pressure sensors. Also, the shown bellows will collapse and unfold if a certain suction is exceeded. In this way is provided an automatic safety against too high suctions as the suction cannot be increased further even if the bellows is extended further.

The pump unit 102 shown in FIGS. 10 and 11 can be manufactured in one single piece for example by blow moulding. The pump unit comprises at one end a spigot for simple connection to the tubing 103.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

The invention claimed is:

1. A breast pump kit comprising: an electrical driving unit and a breast pump collection system, the breast pump collection system being completely separate from the driving unit and configured to be combined to the driving unit by a user, the breast pump collection system being detachable from the driving unit; wherein the breast pump collection system comprises: a breast shield for placing on a breast of a user, a pump unit, and a tubing connecting the breast shield to the pump unit, wherein the pump unit comprises a compartment of a variable volume and in fluid connection to an exterior only via the tubing, wherein the driving unit comprises at least two attachment means spaced apart by a distance that changes with a driving motion of the driving unit, and wherein the pump unit is configured to be detachably combined to the driving unit by placing the pump unit in engagement with the attachment means such that the driving motion of the driving unit acts to alternatingly expand and contract the compartment of the pump unit, the pump unit thereby creating alternating suction and pressure in the breast shield and at the breast of the user when in use; and wherein the pump unit comprises a bellows and is manufactured as a single-unit component.

2. The breast pump kit according to claim 1, wherein the bellows comprises of a number of folds in the interval of 1-30 folds.

3. The breast pump kit according to claim 1, wherein the breast pump collection system comprises two breast shields connected to the same pump unit via tubing.

4. The breast pump kit according to claim 1, wherein the breast pump collection system further comprises a bottle fluidly connected to the breast shield.

5. The breast pump kit according to claim 1, wherein the pump unit is made of a thermoplastic material.

6. The breast pump kit according to claim 1, wherein the pump unit, the tubing and the breast shield are made of the same material.

7. The breast pump kit according to claim 1, wherein the pump unit is manufactured by blow moulding.

8. The breast pump kit according to claim 1, wherein the driving unit comprises a stepper motor.

9. The breast pump kit of claim 1, wherein the breast pump collection system is a single-use disposable product.

10. The breast pump kit according to claim 1, further comprising a control system for controlling the driving unit.

11. The breast pump kit according to claim 10, wherein the control system is configured to control a stroke length of the driving motion of the driving unit.

12. The breast pump kit according to claim 10, wherein the control system is configured to control a frequency of the driving motion of the driving unit.

13. A breast pump collection system for use with an electrical driving unit having at least two attachment means spaced apart by a distance and being configured to be detachably combined to the driving unit wherein the breast pump collection system comprises: a breast shield for placing on a breast of a user, a pump unit, and a tubing connecting the breast shield to the pump unit, wherein the pump unit comprises a compartment of a variable volume and in fluid connection to an exterior only via the tubing, wherein the pump unit is configured to be detachably combined to the driving unit by placing the pump unit in engagement with the attachment means such that a driving motion of the driving unit acts to alternatingly expand and contract the compartment of the pump unit while changing the distance between the attachment means, the pump unit thereby creating alternating suction and pressure in the breast shield and at the breast of the user when in use, wherein the pump unit comprises a bellows and is manufactured as a single-unit component, and wherein the breast pump collection system is configured to be completely separate from the driving unit and configured to be combined to the driving unit by a user.

\* \* \* \* \*

UNITED STATES PATENT AND TRADEMARK OFFICE
CERTIFICATE OF CORRECTION

PATENT NO.       : 10,426,876 B2                                   Page 1 of 1
APPLICATION NO.  : 15/029109
DATED            : October 1, 2019
INVENTOR(S)      : Jan Erik Vest Hansen It is certified that error appears in the above-identified patent and that said Letters Patent is hereby corrected as shown below:

On the Title Page

At (54), and in the Specification, Column 1, Line 1, change "BREST" to --BREAST--.

Signed and Sealed this
Twenty-sixth Day of November, 2019

Andrei Iancu
*Director of the United States Patent and Trademark Office*